US010632271B1

(12) United States Patent
Leevy et al.

(10) Patent No.: US 10,632,271 B1
(45) Date of Patent: Apr. 28, 2020

(54) VERSATILE SUBJECT BED

(71) Applicants:Warren Matthew Leevy, Granger, IN (US); Lucas Liepert, Granger, IN (US); William McLaughlin, South Bend, IN (US)

(72) Inventors: Warren Matthew Leevy, Granger, IN (US); Lucas Liepert, Granger, IN (US); William McLaughlin, South Bend, IN (US)

( * ) Notice: Subject to any disclaimer, the term of this patent is extended or adjusted under 35 U.S.C. 154(b) by 238 days.

(21) Appl. No.: 15/365,708

(22) Filed: Nov. 30, 2016

Related U.S. Application Data

(60) Provisional application No. 62/261,090, filed on Nov. 30, 2015.

(51) Int. Cl.
*A61M 16/01* (2006.01)
*A61G 13/00* (2006.01)
(Continued)

(52) U.S. Cl.
CPC .............. *A61M 16/01* (2013.01); *A61D 7/04* (2013.01); *A61G 10/00* (2013.01);
(Continued)

(58) Field of Classification Search
CPC .... A61M 16/01; A61M 16/104; A61M 16/18; A61M 16/009; A61M 2205/84;
(Continued)

(56) References Cited

U.S. PATENT DOCUMENTS 3,021,840 A * 2/1962 Hallamore .......... A61M 16/104
128/200.21
3,094,101 A 6/1963 Porter
(Continued)

FOREIGN PATENT DOCUMENTS

EP 2095791 9/2009
KR 1020130134699 11/2013
(Continued)

OTHER PUBLICATIONS

Xenogen, XGI-8 Gas Anesthesia System, Product pamphlet obtained from http://www.caliperls.com/assets/015/7293.pdf, copyright 2007 Caliper Life Sciences Inc., obtained from internet Aug. 2, 2019.
(Continued)

*Primary Examiner* — David R Hare
(74) *Attorney, Agent, or Firm* — Notre Dame Intellectual Property Clinic

(57) ABSTRACT

A versatile subject bed for use with one or more test subjects that is configured to keep the subjects sedated throughout either a surgical procedure or imaging process. In embodiments, the subject bed can include interchangeable manifolds allowing the platform to hold up to four subjects at the same time. The interchangeable manifolds can include configurations designed to provide for a single subject, two subjects or four subjects. The four-subject manifold can include an elevated platform that holds two subject side by side and allows the subjects to be stacked during imaging or other procedures. The subject bed can also incorporate an integrated anesthesia channel. Various embodiments include a docking mechanism for easy connection of anesthesia to the platform, as well as an adapter for fitting smaller or multiple subjects simultaneously within the subject bed.

15 Claims, 16 Drawing Sheets

(51) Int. Cl.
  *A61G 13/10* (2006.01)
  *A61M 16/00* (2006.01)
  *A61G 10/00* (2006.01)
  *A61D 7/04* (2006.01)

(52) U.S. Cl.
  CPC ......... *A61G 13/0018* (2013.01); *A61G 13/10* (2013.01); *A61M 16/009* (2013.01); *A61M 2205/84* (2013.01)

(58) Field of Classification Search
  CPC .... A61G 13/10; A61G 13/0018; A61G 10/00; A61D 7/00; A61D 7/04
  See application file for complete search history.

(56) References Cited

U.S. PATENT DOCUMENTS

| | | | |
|---|---|---|---|
| 3,230,577 A * | 1/1966 | Hughes | A22B 3/00 128/205.25 |
| 3,367,308 A * | 2/1968 | Quattrone | A01K 1/031 119/420 |
| 3,813,092 A * | 5/1974 | Foster | A61M 16/009 128/200.24 |
| 3,838,687 A * | 10/1974 | Mosher | A61B 6/045 128/200.11 |
| 4,064,877 A * | 12/1977 | Moscowitz | A61D 7/04 128/202.13 |
| 4,332,244 A * | 6/1982 | Levy | A61D 7/04 128/205.25 |
| 4,520,808 A * | 6/1985 | LaBauve | A01K 13/001 128/200.14 |
| 4,721,060 A * | 1/1988 | Cannon | A61D 7/04 119/420 |
| 4,787,382 A * | 11/1988 | Pekovic | A61D 7/04 119/421 |
| 4,860,741 A * | 8/1989 | Bernstein | A61D 7/04 128/204.18 |
| 5,044,363 A * | 9/1991 | Burkhart | A61M 16/009 128/201.25 |
| 5,297,502 A * | 3/1994 | Jaeger | A01K 1/031 119/420 |
| 5,626,130 A | 5/1997 | Vincent et al. | |
| 5,896,829 A | 4/1999 | Rothenberg et al. | |
| 5,899,846 A * | 5/1999 | Sternberg | A61G 10/026 128/202.12 |
| 6,131,571 A * | 10/2000 | Lampotang | A61M 16/00 128/204.18 |
| 6,275,650 B1 * | 8/2001 | Lambert | A61M 16/18 128/203.12 |
| 6,349,725 B1 * | 2/2002 | Perkins | A61D 7/04 128/206.21 |
| 6,352,076 B1 * | 3/2002 | French | A61D 7/04 119/420 |
| 6,776,158 B1 * | 8/2004 | Anderson | A01K 1/031 119/416 |
| 7,021,483 B2 | 4/2006 | Tack et al. | |
| 7,464,707 B2 | 12/2008 | Dalgetty et al. | |
| 7,503,323 B2 * | 3/2009 | Dalgetty | A01K 1/031 128/203.12 |
| 7,865,226 B2 | 1/2011 | Chiodo | |
| 7,997,268 B1 * | 8/2011 | Leonard | A61D 7/04 128/203.12 |
| 8,186,305 B2 * | 5/2012 | Kawano | A61D 7/04 119/420 |
| 8,189,737 B2 | 5/2012 | Keller et al. | |
| 8,196,574 B2 * | 6/2012 | Ichikawa | A61D 7/04 119/420 |
| 8,342,136 B2 | 1/2013 | Hadjioannou et al. | |
| 8,660,633 B2 | 2/2014 | Zagorchev et al. | |
| 8,851,018 B2 | 10/2014 | Rapoport et al. | |
| 8,862,201 B2 | 10/2014 | Zagorchev et al. | |
| 8,918,163 B2 | 12/2014 | Yared et al. | |
| 9,820,675 B2 | 11/2017 | Rapoport et al. | |
| 2004/0136878 A1 | 7/2004 | Meier et al. | |
| 2004/0216737 A1 * | 11/2004 | Anderson | A01K 1/031 128/203.12 |
| 2006/0011143 A1 * | 1/2006 | Drummond | A01K 1/031 119/420 |
| 2008/0271736 A1 * | 11/2008 | Leonard | A61D 7/04 128/203.12 |
| 2009/0151720 A1 * | 6/2009 | Inoue | A22B 3/00 128/203.12 |
| 2010/0101500 A1 | 4/2010 | Sannie et al. | |
| 2010/0269260 A1 | 10/2010 | Lanz | |
| 2011/0162652 A1 * | 7/2011 | Rapoport | A61D 7/04 128/205.26 |
| 2011/0186049 A1 * | 8/2011 | Rapoport | A61M 16/1075 128/203.29 |
| 2012/0073509 A1 | 3/2012 | Rapoport et al. | |
| 2012/0216807 A1 * | 8/2012 | Dunlop | A61D 7/04 128/203.29 |
| 2012/0278990 A1 | 11/2012 | Lanz et al. | |
| 2014/0069426 A1 | 3/2014 | Flouts et al. | |
| 2014/0121493 A1 | 5/2014 | Shi et al. | |
| 2014/0128880 A1 * | 5/2014 | Gandola | A01K 11/00 606/116 |
| 2014/0378821 A1 | 12/2014 | Rapoport et al. | |
| 2014/0378825 A1 | 12/2014 | Rapoport et al. | |
| 2015/0047724 A1 * | 2/2015 | Leevy | A61D 7/04 137/561 A |
| 2015/0320534 A1 | 11/2015 | Im et al. | |
| 2015/0327968 A1 * | 11/2015 | Im | A61D 3/00 119/756 |
| 2015/0328065 A1 | 11/2015 | Boak | |
| 2016/0120723 A1 * | 5/2016 | Giulianotti | A61G 10/005 600/21 |
| 2017/0035982 A1 * | 2/2017 | Roseman | A61M 16/01 |
| 2017/0259024 A1 * | 9/2017 | Chen | A61M 16/104 |
| 2017/0312006 A1 * | 11/2017 | McFarlin | A61N 1/36 |

FOREIGN PATENT DOCUMENTS

| | | |
|---|---|---|
| WO | WO19999017678 | 4/1999 |
| WO | 1999043389 | 9/1999 |
| WO | 2007135248 | 11/2007 |
| WO | WO2010002331 | 1/2010 |

OTHER PUBLICATIONS

EZ-Systems, EZ-109 Multi-Animal Breather, https://www.ersystemsinc.com/product/ez-109-multi-breather/ website, copyright 2019 EZ-Systems, obtained from internet Aug. 3, 2019.

Parkland Scientific, Multi Station Surgical Board, parklandscientific.com website, copyright 2019 Parkland Scientific, obtained from Internet Aug. 2, 2019.

MI Labs B.V., Accessories web page, milabs.com website, copyright 2018 MILabs B.V., obtained from the internet Mar. 2, 2019.

Jun Dazai, Nicholas A. Bock, Brian J. Nieman, Lorinda M. Davidson, R. Mark Henkelman, and X. Josette Chen, Multiple Mouse Biological Loading and Monitoring System for MRI, Magnetic Resonance in Medicine, 2004, 52:709-715 (2004).

Chris Suckow, Claudia Kuntner, Patrick Chow, Robert Silverman, Arion Chatziioannou, and David Stout, Multimodality Rodent Imaging Chambers for Use Under Barrier Conditions With Gas Anesthesia, Mol. Imaging Biol. Mar.-Apr. 2009; 11(2) 100-106.

* cited by examiner

VERSATILE SUBJECT BED

CROSS-REFERENCE TO RELATED APPLICATIONS

This application claims the benefit of the filing date of U.S. provisional patent application Ser. No. 62/261,090, filed on Nov. 30, 2015, entitled "Versatile Inhalation Anesthesia Platform for Small Animal Surgery and/or Imaging," the disclosure of which is incorporated herein by reference.

BACKGROUND

In-vivo imaging of animal subjects is a common part of research and investigation of the biological functions of subjects. One advantage of in-vivo imaging is the ability to repeatedly scan or image subjects, allowing comparisons over time as well as comparisons between individual subjects. Repeated scanning of a single subject, or a limited set of subjects, facilitates identification of trends and may be more efficient and effective than single instance scanning of numerous subjects. However, comparison of images can be difficult with live subjects as positions may vary from scan to scan and motion of a subject during scanning negatively impacts the resulting images.

In-vivo imaging typically requires the subject to remain motionless during the scanning process, which can take up to an hour or more, depending upon the number and type of images collected. Injected anesthetics may be insufficient to restrain the subject for the entire length of the scanning process. Moreover, injected anesthetics vary in depth over time, which could effect the very biological functions being investigated. Consequently, anesthetic gas or fluid can be used to provide a constant depth of anesthesia to the subject. However, delivery of the anesthetic gas while the subject is within the imaging system poses its own challenges.

Typically, imaging beds or subject beds are used to position the subject during imaging, providing a consistent platform for the subject. All or a portion of the subject bed is inserted with the subject in place into the imaging system. As used herein, the term "imaging system" refers to any system used for collecting information about the subject. Imaging systems frequently use an isotope to assist in the creation of an image. Some imaging systems currently in use include, but are not limited to, radiological imaging systems, nuclear imaging systems and optical imaging systems, including but not limited to, Positron Emission Tomography (PET), Computerized Tomography (CT), and Magnetic Resonance Imaging (MRI) system, such as the Albira MicroPET, MicroSPECT, Scanlo VivaCT, Bruker and PerkinElmer MR, IVIS optical imaging systems.

Often in research, it would be beneficial to sedate multiple laboratory animals at once; this is especially true in the field of preclinical optical imaging where a control cohort is compared to an experimental cohort. Additionally, sedation of subjects is typically necessary for performance of surgical procedures. This multiple animal sedation is currently achieved in a number of ways, most commonly focusing on the delivery of the gaseous anesthetic to the nose or mouth of the lab animals through individual nose-cones. The laboratory animals are positioned with their noses propped in these cones so that as they breathe, they inhale the anesthetic gas. The fluid or vapors frequently escape from the nose cones, and leak into the atmosphere, which poses health concerns for those working with these systems and the environment.

BRIEF SUMMARY

The following presents a simplified summary in order to provide a basic understanding of some aspects of the claimed subject matter. This summary is not an extensive overview. It is not intended to either identify key or critical elements or to delineate the scope of the claimed subject matter. Its sole purpose is to present some concepts in a simplified form as a prelude to the more detailed description that is presented later.

In embodiments, a subject bed supports a subject, the subject bed comprising a base having a bed surface on which the subject is positioned; an anesthesia channel integrated into the base that receives an anesthesia fluid from an anesthesia fluid source; and an interchangeable manifold configured to be removably attached to the base. The interchangeable manifold has at least one subject interface in fluid communication with the anesthesia channel, and the subject interface has an anesthesia outlet configured to deliver the anesthesia fluid to the subject positioned on the bed surface. In embodiments, the interchangeable manifold is attached to the base by a magnet and can be replaced by a second interchangeable manifold to configure the subject bed for an additional subject. In embodiments, the interchangeable manifold is a two-subject manifold and the two-subject manifold is configured for side-by-side positioning of the subject and a second subject.

In another embodiment, the interchangeable manifold is a four-subject manifold and the subject bed comprises an elevated stage configured to support two additional subjects and the four-subject manifold is configured to support a two-by-two array of subjects. The elevated stage is connected to a slot in the four subject manifold.

In other embodiments, an exhaust channel is integrated into the base, and the subject interface further comprises an exhaust inlet in fluid communication with the exhaust channel, where negative pressure is applied to the exhaust channel to create a vacuum. The exhaust inlet is proximate to the edge of the subject interface and the subject interface is self-scavenging.

In other embodiments, the subject bed includes a temperature control feature and at least one fiducial receptacle shaped to receive a removable fiducial. In another embodiment, the subject bed includes at least one anchor point attached to the base and configured to secure the subject, and the bed surface includes a removable transparent tray.

In another embodiment, a subject bed supports at least one subject, the subject bed comprising: a base having a bed surface on which the at least one subject is positioned and an anesthesia channel integrated into the base; a connector that connects an anesthesia fluid source and the anesthesia channel; a first detachable manifold having a first subject interface connected to the anesthesia channel, the interchangeable manifold is configured to be removably detach from the base to be replaced by a second detachable manifold having a second and third subject interface. Here, each of the first, second and third subject interfaces include an anesthesia outlet that delivers anesthesia fluid to the at least one subject. The second detachable manifold is a four-subject manifold configured to support four subjects. The subject bed also includes an elevated stage configured to support two subjects side-by-side.

To the accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

BRIEF DESCRIPTION OF THE DRAWINGS

The systems, devices and methods may be better understood by referring to the following description in conjunction with the accompanying drawings, in which like numerals indicate like structural elements and features in various figures. The components in the figures are not necessarily to scale, and simply illustrate the principles of the systems, devices and methods. The accompanying drawings illustrate only possible embodiments of the systems, devices and methods and are therefore not to be considered limiting in scope.

DETAILED DESCRIPTION

Aspects of the system and methods are described below with reference to illustrative embodiments. The references to illustrative embodiments below are not made to limit the scope of the claimed subject matter. Instead, illustrative embodiments are used to aid in the description of various aspects of the systems and methods. The description, made by way of example and reference to illustrative reference is not meant to being limiting as regards any aspect of the claimed subject matter.

There are two primary scenarios in which a pre-clinical researcher will commonly use anesthesia on a living subject, such as a mouse or rat; during a surgical procedure or during imaging of the subject. The subject bed 100 described herein is designed to handle both applications either separately or together, such as when a subject undergoing surgery requires imaging. Embodiments of the subject bed 100 provide a platform that can be easily transferred from the benchtop to an imaging system and back again.

The subject bed 100 described herein can be used in conjunction with existing sources of fluids and negative pressure to evenly distribute anesthetize one or more subjects. As used herein, "subject" refers to a small animal such as a laboratory rodent. As used herein, "fluid" refers to a gas, vapor, liquid, or aerosol. The terms "subject bed" and "bed" are used interchangeably. In embodiments, the described subject beds 100 are used to deliver anesthetic gases or fluids, including but not limited to isoflurane, to sedate a subject or subjects for imaging or surgical procedures.

Figure 1A:
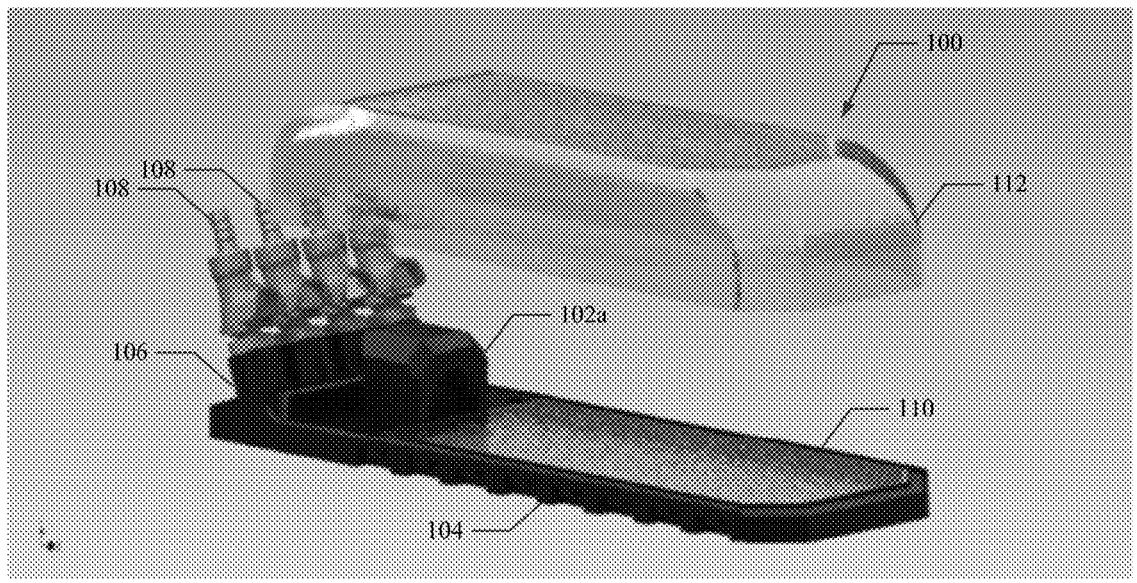
FIG. 1a depicts a perspective view of an embodiment of a subject bed with a single subject interchangeable manifold.
Figure 1B:
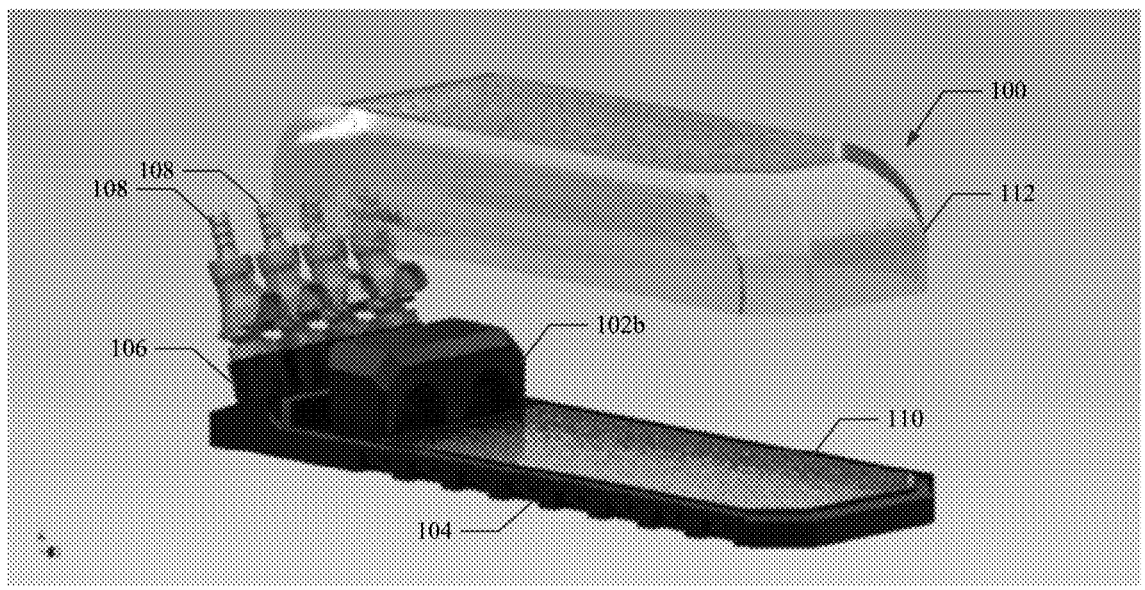
FIG. 1b depicts a perspective view of the subject bed of FIG. 1a with a two-subject interchangeable manifold.
Figure 1C:
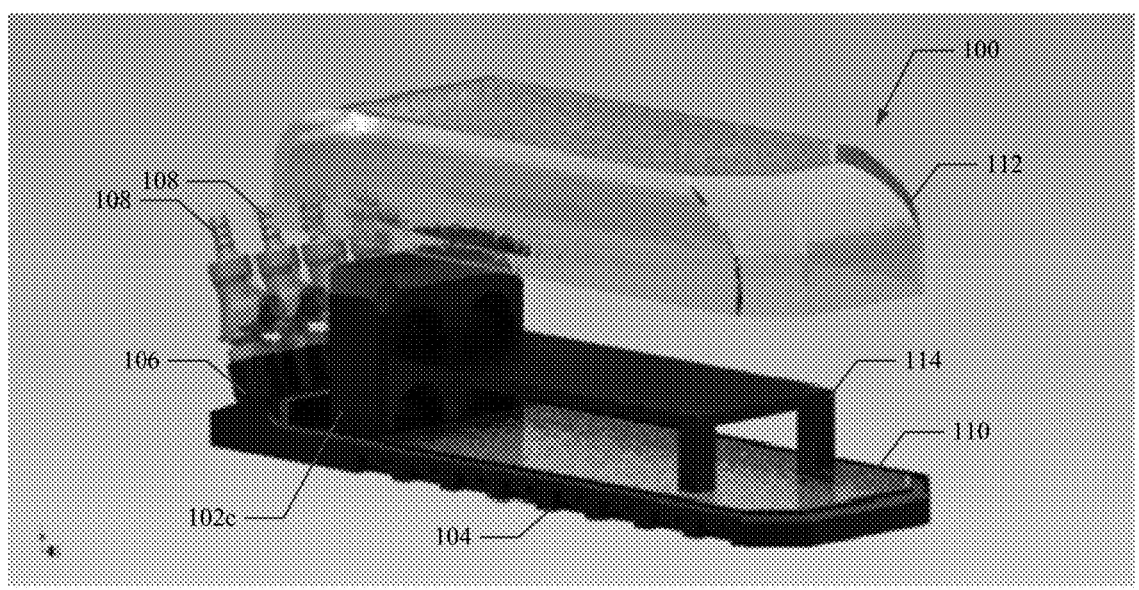
FIG. 1c depicts a perspective view of the subject bed of FIG. 1a with a four-subject interchangeable manifold.

Referring to FIGS. 1a-1c, embodiments of a subject bed 100 including an interchangeable manifold 102a, 102b, 102c are depicted. The illustrated subject bed 100 can be used to support one or more subjects for surgical procedures, in-vivo imaging, and the like, while delivering anesthesia fluid to the subject. In most optical imaging instruments, the amount of functional space is limited; therefore, any obstructions of this space are undesirable. Embodiments of the subject bed 100 described herein utilize a set of compact and interchangeable manifolds 102a, 102b, 102c and integrated anesthesia delivery channels to reduce the bulk of the subject bed 100, increase the amount of functional space of the imaging instrument that can be utilized, and rapidly accommodate the subjects based on the experimental parameters.

In embodiments, the subject bed 100 includes a base 104 that supports the subject or subjects, a connector portion 106 that includes and one or more connectors 108 capable of attaching to sources of negative pressure, anesthesia fluid, or other fluids. In embodiments, connectors 108 include one or more tube clips for conveniently securing tubes bringing warmed fluid and anesthesia to, or drawing exhaust fluid from, the subject bed 100. Tube clips can keep tubes organized and close to the connector portion 106, making it less likely that the tubes will be snagged, torn, kinked, or otherwise disturbed. The base 104 can include one or more channels 800 that link the connectors 108 to the interchangeable manifold 102a, 102b, 102c, where the channels 800 deliver the fluid or fluids to the subject or subjects via the interchangeable manifold 102a, 102b, 102c. As used herein, the term "channel" denotes a conduit or connector and is not necessarily tubular in nature.

As shown, in embodiments the base 104 includes a bed surface 110 that is generally flat and all or a portion of the bed surface 110 can be transparent. This transparent embodiment of the bed surface 110 is particularly useful for optical imaging of the subject as it allows the subject to be viewed or imaged through the bed surface 110 from below with little or no obstructions. The illustrated subject bed 100 also includes a cover 112 that can assist in containing anesthesia fluid to the subject bed 100. In addition, the cover 112 can retain warm air around the subject, particularly if the subject bed 100 includes a heating means. In addition, the cover 112 can retain the subject itself, should the subject wake from anesthesia. The cover 112 can rest on the bed surface 110 and may form a seal to retain air or fluids within the subject bed 100. In other embodiments, the subject bed 100 can be used without a cover 112. The anesthetic gas is retained proximate to the subject interface 200 by an exhaust or scavenging system described below, which prevents the anesthetic gas from dissipating into the lab atmosphere.

Figure 2:
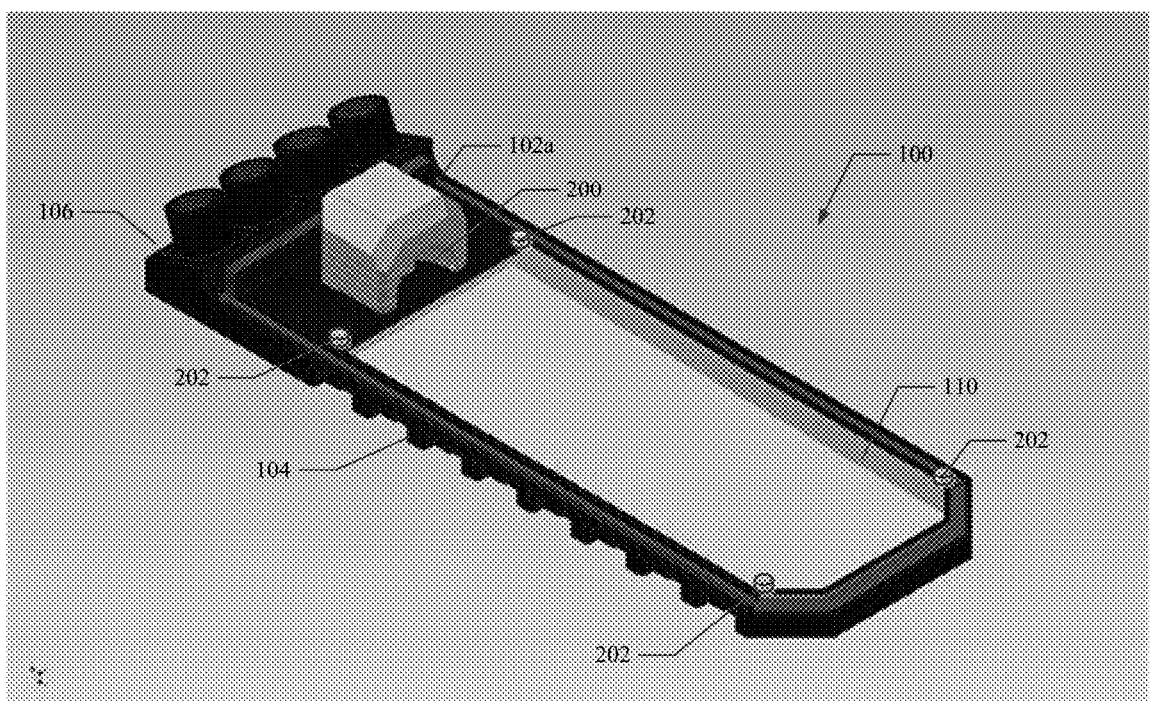
FIG. 2 depicts a perspective view of an embodiment of a subject bed and a single subject interchangeable manifold.
Figure 4:
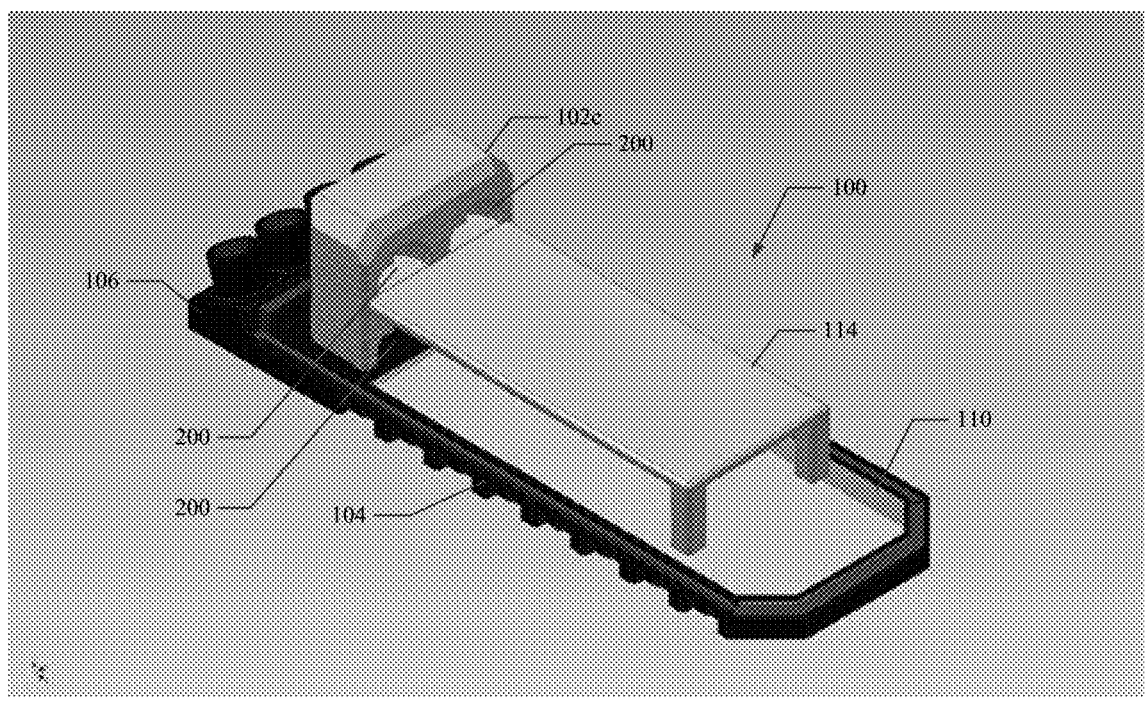
FIG. 4 depicts a perspective view of an embodiment of the subject bed with an interchangeable manifold for up to four subjects and an elevated stage.

The subject bed 100 can include one or more interchangeable manifolds 102a, 102b, 102c that can be selected, attached, or detached depending upon the number of subjects to be retained in the subject bed 100. For example, as shown in FIG. 1a and FIG. 2, the interchangeable manifold 102a, 102b, 102c can be a single subject manifold 102a, designed to deliver anesthesia to a single subject at a time. Alternatively, as shown in FIG. 1b, an interchangeable manifold 102b can be selected and used to deliver anesthesia to two subjects at the same time, where the subjects are positioned side-by-side on the bed surface 110. An exemplary configuration of a four-subject interchangeable manifold 102c is shown in FIGS. 1c and 4. Here, the interchangeable manifold 102c can deliver anesthesia to up to four subjects at the same time. The four-subject manifold 102c is shown with an elevated stage 114 that supports up to two subjects. In embodiments, the interchangeable manifold 102a, 102b, 102c can be swapped out, based upon the desired number of test subjects, and provides a versatile subject bed 100. The illustrated subject bed 100 is streamlined, and can be used for surgical procedures, such as on the research bench as well as with an imaging device.

Figure 3:
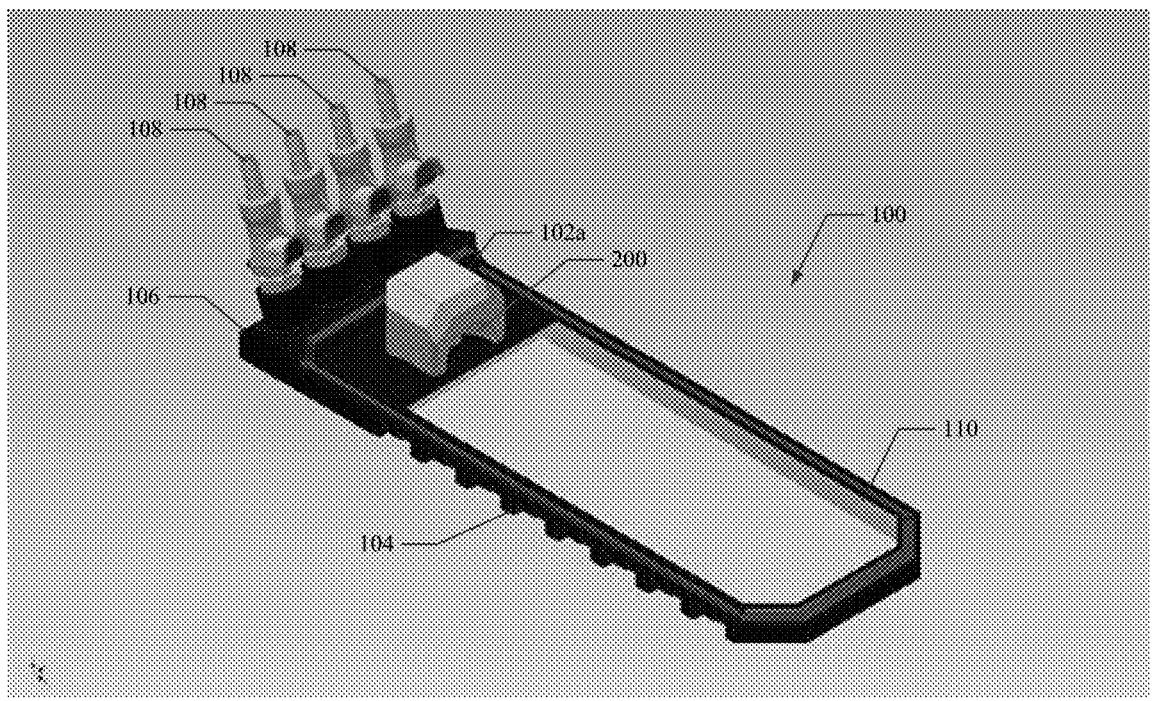
FIG. 3 depicts a perspective view of another embodiment of the subject bed with a single subject interchangeable manifold and connectors.

In embodiments, each of the interchangeable manifolds 102a, 102b, 102c includes one or more subject interfaces 200, more easily seen in FIGS. 2-4, configured to deliver anesthesia to subjects. The subject interfaces 200 are described below in greater detail with respect to FIGS. 5a, 5b, 6a and 6b. The interchangeable nature of the manifolds 102a, 102b, 102c allows the appropriate manifold 102a, 102b, 102c to be used with the correct number of subjects and reduces waste. For example, when only a single subject is to be imaged, the anesthesia fluid can be delivered solely to that subject without waste that can occur if a multiple subject manifold 102b, 102c is used for a single subject.

Generally, the subject will be sedated throughout the entire scanning period or surgical procedure. To maintain sedation, anesthesia is continually delivered to the subject throughout the imaging or surgical procedure. To avoid over-sedation or suffocation, the chamber of the subject bed 100 or the manifold 102a, 102b, 102c can be connected to a vacuum line to draw out excess carbon dioxide and anesthesia gas as fresh air and additional anesthesia are delivered. During the imaging process conventional subject beds can become saturated with anesthesia, and if the anesthesia is not properly exhausted, the anesthesia will remain in the chamber of the subject bed 100 after the conclusion of the imaging process. This results in potentially exposing lab workers to the anesthesia when the subject is removed from the chamber of the subject bed 100. Repeated exposure to the anesthesia may have adverse health effects both on the subject and the lab worker. Further, flooding the entire subject bed chamber with the anesthesia gas is an inefficient use of anesthesia, raising the costs of the imaging process.

The subject beds 100 described herein can reduce or minimize the escape of excess anesthesia fluid from the interchangeable manifolds 102a, 102b, 102c. Escaping fluids can pose health concerns for the animal subjects as well as the human operators. Embodiments of the described subject beds 100 can scavenge the fluid before it leaves the subject interface 200, thereby reducing the risk of harm to both humans and animal subjects.

Additional embodiments of the subject bed 100 incorporate temperature control features that maintain the bed 100 and subjects at a steady temperature during the imaging process. When sedated, the subjects have a reduced capacity to regulate their body temperature, resulting in decreased blood flow and increased risk of hypothermia. Decreased blood flow is especially problematic when the target of imaging (e.g. biomarker) is reliant on normal blood flow. Embodiments of subject beds 100 disclosed herein maintain the body temperature of the subject avoiding the detrimental effects of heat loss in the imaging subject.

As shown in FIGS. 1a-1c, in embodiments, the subject bed 100 includes a cover 112 that forms the top portion of a chamber enclosing the subject and anesthesia. In embodiments the cover 112 rests in a rabbet in the upper surface of the base 104. In other embodiments, the cover 112 is attached to the base 104 via a hinge or other mechanism that allows access to the bed surface 110 to insert or position the subject within the chamber. The chamber is opened to insert, remove or access to the subject. In embodiments, the cover 112 and base 104 form a seal that prevents the anesthetic gas from escaping the chamber 104.

In addition, as illustrated in FIGS. 2-4 the bed surface 110 can include a transparent portion that facilitates optical imaging of the subject from below the base 104 of the subject bed 100. However, when the four-subject manifold 102c is used with the elevated stage 114, shown in FIG. 4, the transparent portion will be less effective due to obstruction of the view of the top subjects by the elevated stage 114 and the subjects on the bed surface 110. The transparent portion can be implemented as a transparent removable tray. The removable tray can facilitate quick transition between sets of subjects without changing the manifold 102a, 102b, 102c or fluid connections during a series of surgical procedures or imaging of subjects.

In other embodiments, the bed surface 110 or base 104 can include anchor points 202 that assist in securing or immobilizing the subject or subjects. Delicate surgical procedures or detailed scanning are more effective when the subject remains still throughout the procedure or image scanning. Anchor points 202 can be implemented in a variety of ways, including but not limited to simple posts or bars to which the subject can be attached. In other embodiments the base 104 or the manifold 102a, 102b, 102c can include stereotactic devices for the head of the subject. For stereotactic surgery a three-dimensional coordinate system is used to locate targets inside the body of the subject. Here, the manifold 102a, 102b, 102c or base 104 can provide a reliable frame of reference when the subject is secured to the subject bed 100. In embodiments one or more clamps or bars can retain the head or other part of the subject in a fixed position. A commercially available stereotactic system can be used with the subject bed 100.

FIG. 3 shows an embodiment of a subject bed 100 with a single subject interchangeable manifold 102a and a set of connectors 108. These connectors 108 can be attached to the connecting portion 106 in any suitable manner, such as threaded connector, or quick connector that allows the connectors 108 to be removably attached to the connecting portion. Each of the connectors 108 can be connected to source of negative pressure or a fluid. For example, a first connector can be attached via a hose or flexible tubing to a source for fluid anesthesia. In embodiments, the connectors 108 include a valve that controls flow of the fluid.

Figure 5A:
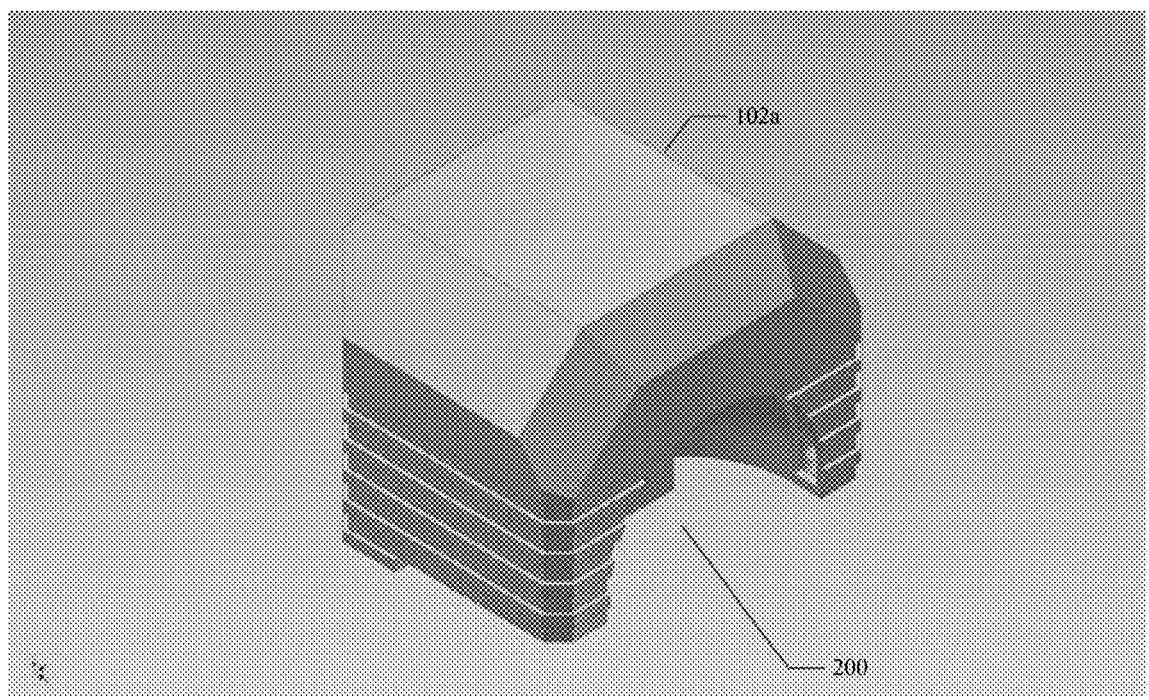
FIG. 5a depicts a perspective view of an embodiment of an interchangeable manifold for use with a single subject.
Figure 5B:
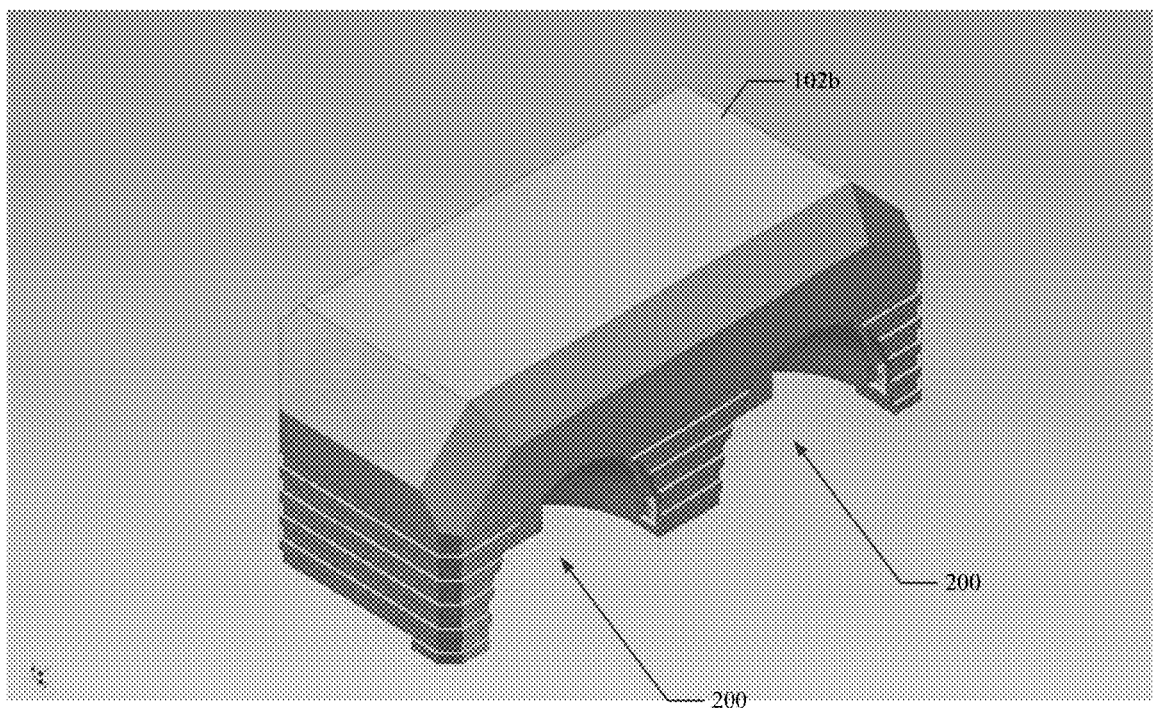
FIG. 5b depicts a perspective view of an embodiment of an interchangeable manifold for use with two subjects.

FIGS. 5a-5d provide perspective views of various configurations of the interchangeable manifold 102a, 102b, 102c. A single subject manifold 102a is shown in FIG. 5a, where the manifold 102a includes a single subject interface 200. The depicted manifold 102a can be removably attached to the base 104 such that it connects to the channel or channels 800 that deliver anesthesia fluid to the subject interface 200. The subjects nose or muzzle is then positioned within the cavity of the subject interface 200 to anesthetize the subject. In FIG. 5b, a two-subject manifold 102b is shown. As with the single subject manifold 102a, the two-subject manifold 102b is removably attached to the base 104 of the subject bed 100. Lumina 700 within the manifold 102b deliver the anesthesia from the base 104 to each of the subject interfaces 200 to anesthetize the two subjects positioned beside each other on the bed surface 110.

Figure 5C:
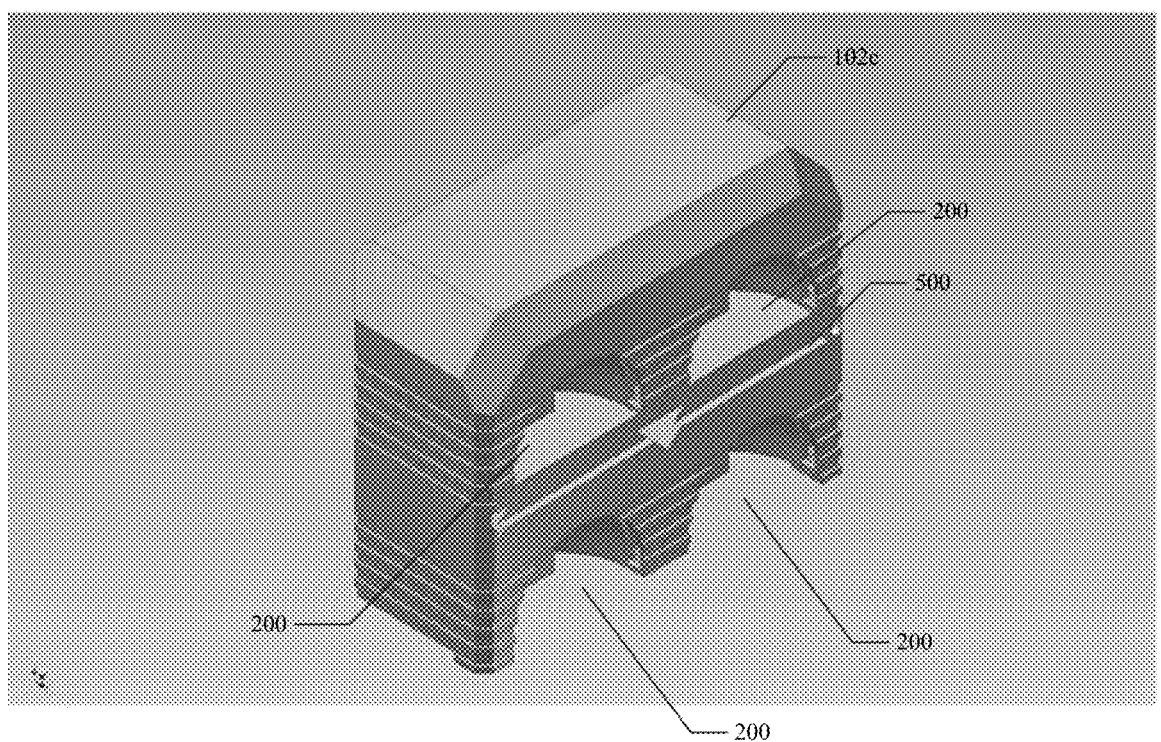
FIG. 5c depicts a perspective view of an embodiment of an interchangeable manifold for use with up to four subjects.
Figure 5D:
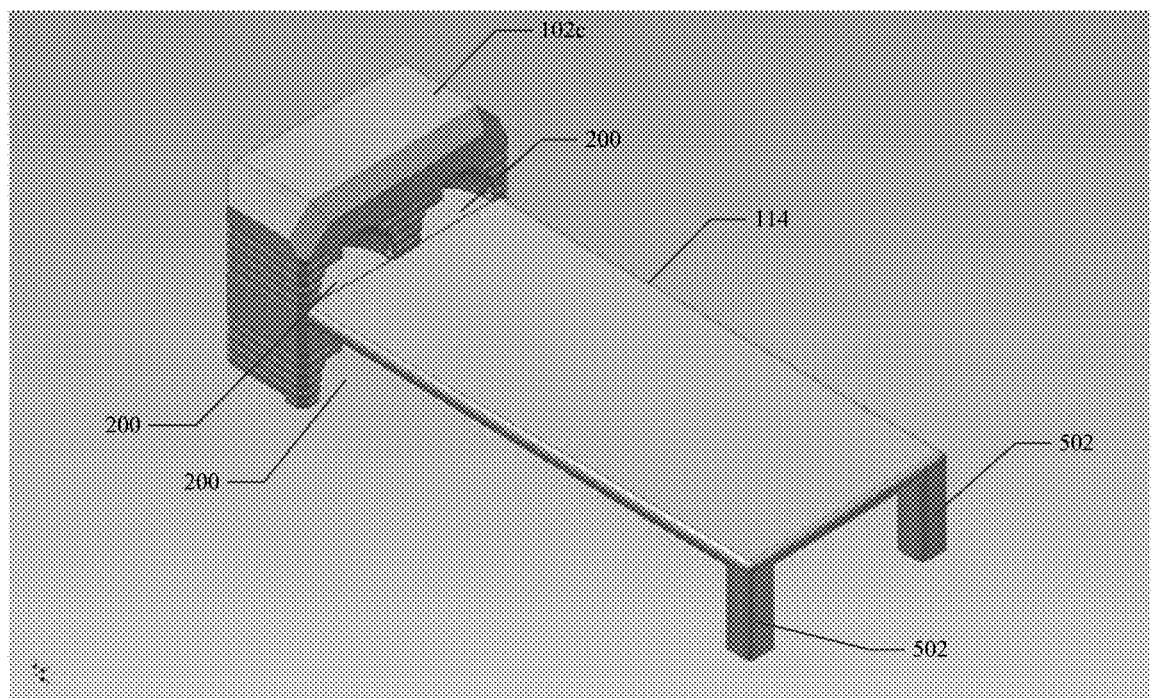
FIG. 5d depicts a perspective view of an embodiment of an interchangeable manifold for use with up to four subjects with an attached elevated stage.

FIGS. 5c and 5d depict the four-subject manifold 102c with four separate subject interfaces 200 arranged in a two-by-two array, where two subjects are placed side-by-side on the bed surface 110 and the other two subjects are placed side-by-side on the elevated stage 114. To fit in a conventional imaging system, the subject bed 100 can be limited in its dimensions and depending upon the size of the subjects. It may not be feasible to simply place four test subjects side-by-side on the bed surface 110. To overcome this potential problem, the four-subject manifold 102c incorporates, or can be used in conjunction with, an elevated stage 114 or platform that positions two of the subject over top of the two subject resting on the bed surface 110. In embodiments, the elevated stage 114 has one or more legs 502 that support the stage surface. In the depicted embodiment, the stage surface can be inserted into a slot 500 in the four-subject manifold 102c to connect the stage 114 to the manifold 102c. This connection can be helpful in maintaining stability of the elevated stage 114 during the imaging process or when moving the platform with elevated stage 114 and interchangeable interface. In other embodiments, the elevated stage 114 can include magnets or other methods to secure the stage 114 to the base 104.

Figure 6A:
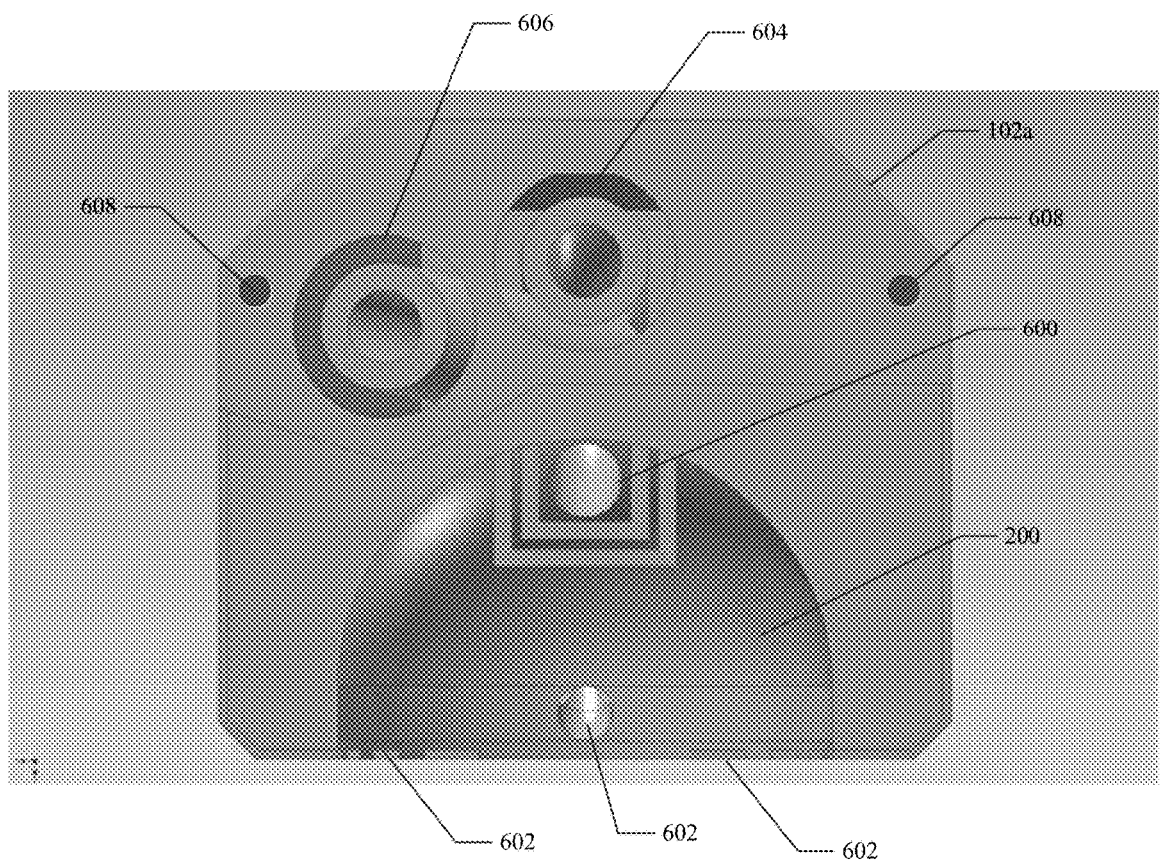
FIG. 6a depicts a bottom view of an interchangeable manifold for use with a single subject.
Figure 6B:
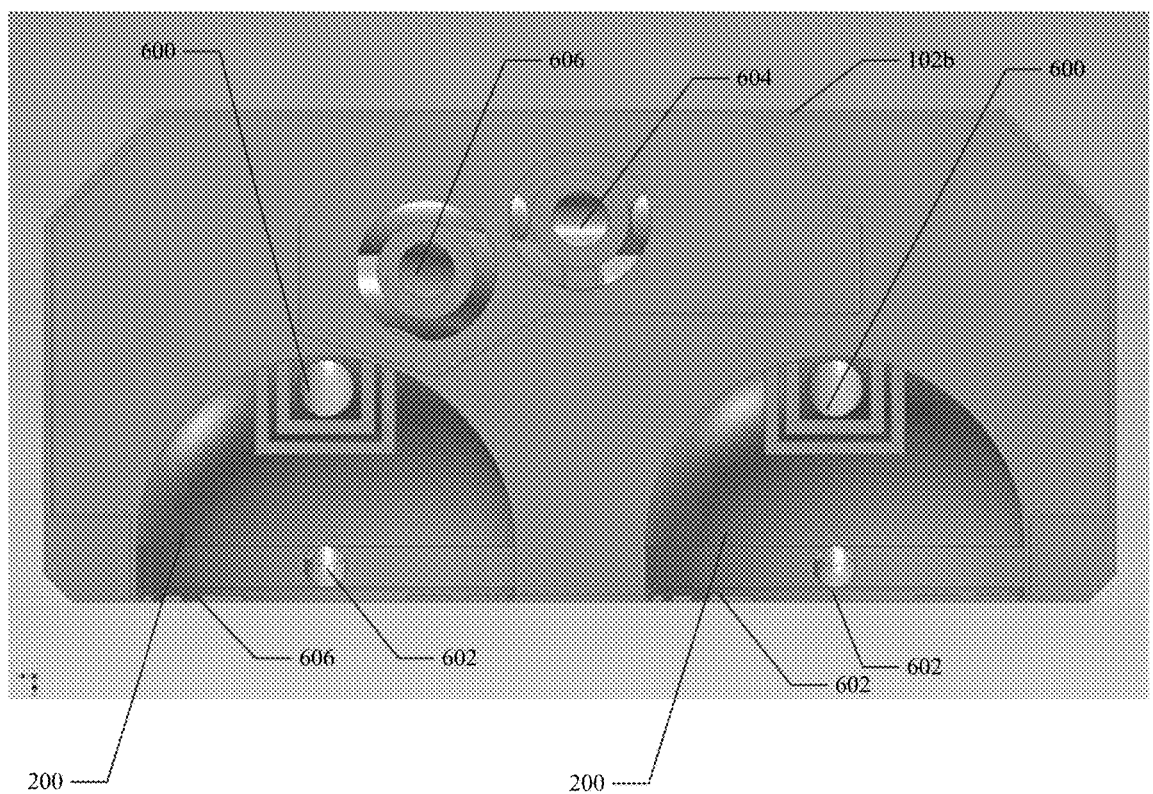
FIG. 6b depicts a bottom view of an interchangeable manifold for use with two subjects.

FIGS. 6a and 6b depict bottom views of the single subject and two-subject manifolds 102a, 102b respectively. These figures provide a clear view of embodiments of the subject interface 200, which can be implemented as a self-scavenging interface that controls the flow of anesthesia through use of an exhaust inlet or inlets 602. Anesthesia flows into the manifold 102a, 102b, 102c from a channel 800 in the base 104 via the anesthesia port 604 of the manifold 102a, 102b, 102c. From the anesthesia port 604 the anesthesia is directed via a lumen 700, shown in FIGS. 7a, 7b and 7c, to an anesthesia outlet or outlets 600. Similarly, negative pressure flows form a channel in the base 104 to the exhaust port 606 in the manifold 102a, 102b, 102c and through a lumen 702 to the exhaust inlet or inlets 602 in the subject interface 200 or interfaces.

As depicted, each subject interface 200 includes an anesthesia outlet 600 in the interior of the subject interface 200 that delivers the anesthesia fluid to the nose or muzzle of the subject. Once the fluid has been delivered to the subject interface 200, it can be inhaled by a subject, and the amount of fluid or mixture of fluids can be carefully controlled by external means, including but not limited to, an anesthesia delivery system, a valve or flow regulator.

In embodiments, the subject interface 200 includes one or more exhaust inlets 602 connected via the lumen 702 and the channel 800 in fluid communication with an exhaust connector connected to a source of negative pressure, such as through a hose, or hose adapter. When a negative pressure is applied to the exhaust connector, fluid is drawn in from the subject interface 200 through the exhaust inlet 602 and channel and out of the manifold 102a, 102b, 102c. The drawing of fluid through the exhaust inlet 602 will minimize or prevent the fluid from escaping the subject interface 200. This self-scavenging subject interface 200 reduces potential exposure of lab personnel to the anesthesia.

The rate of flow at each subject interface 200 can be controlled simultaneously by adjusting the flow upstream from the anesthesia. Such adjustment can be accomplished by various means including, but not limited to, an anesthesia delivery system, a valve, or a flow regulator. When the number of subject interfaces 200 exceeds the number of subjects, it is not necessary to block off the unused subject interfaces 200, because the negative pressure will draw any delivered fluid from the empty subject interfaces 200 regardless of the presence of a subject. This allows a desired flow rate to be maintained without having to adjust for the number of subjects present for a particular procedure or imaging.

In embodiments, the subject interfaces 200 are formed as cavities in the manifold 102a, 102b, 102c, sized to receive the nose of the intended subject animal. In the illustrated embodiment, the subject interface 200 intersects the bottom and an adjacent face of the manifold 102a, 102b, 102c, creating an aperture to receive the nose of the subject animal. The bed surface 110 on which the manifold 102a, 102b, 102c is placed forms a bottom to the cavity in the single and two-subject manifolds 102a, 102b, as well as in the bottom two subject interfaces 200 in the four-subject manifold 102c. This design allows the manifold 102a, 102b, 102c to be placed over, or removed from subject animals without disturbing their position. The cavity design of the subject interface 200 can reduce the amount of functional space of the imaging instrument that is taken up by the manifold 102a, 102b, 102c. Additionally, since the subject interface 200 is a cavity rather than a separate cone, material costs can be reduced.

The interchangeable manifold 102a, 102b, 102c can include one or more magnets 608 that secure the manifold 102a, 102b, 102c to the base 104. In certain embodiments, one or more magnets 608 can be incorporated in or near the bottom of the manifold 102a, 102b, 102c. As one skilled in the art will understand, the magnets 608 may be installed in many ways as may be required and/or desired in certain embodiments. For example, the magnets 608 can be affixed to the interior of the manifold 102a, 102b, 102c by adhesive or physical hold-downs. Magnets 608 can improve the seal between the manifold 102a, 102b, 102c and a magnet compatible work surface or plate in the base 104 by holding tight to the surface via magnetism. As used herein, "magnet compatible" refers to material capable of adhering to a permanent magnet, such as a paramagnetic or a ferromagnetic material. A tighter seal minimizes the escape of fluid from the subject interface 200 by reducing potential for fluid to leak between the bed surface 110 and the manifold 102a, 102b, 102c. Stronger magnets, such as rare earth magnets, can result in stronger magnetic attractions. In addition to magnets 608 any other suitable method of removably attaching the manifold 102a, 102b, 102c to the base 104 can be used. For example, the manifold 102a, 102b, 102c could include one or more protrusions or pegs that could be inserted into apertures or slots in the base 104.

Figure 7A:
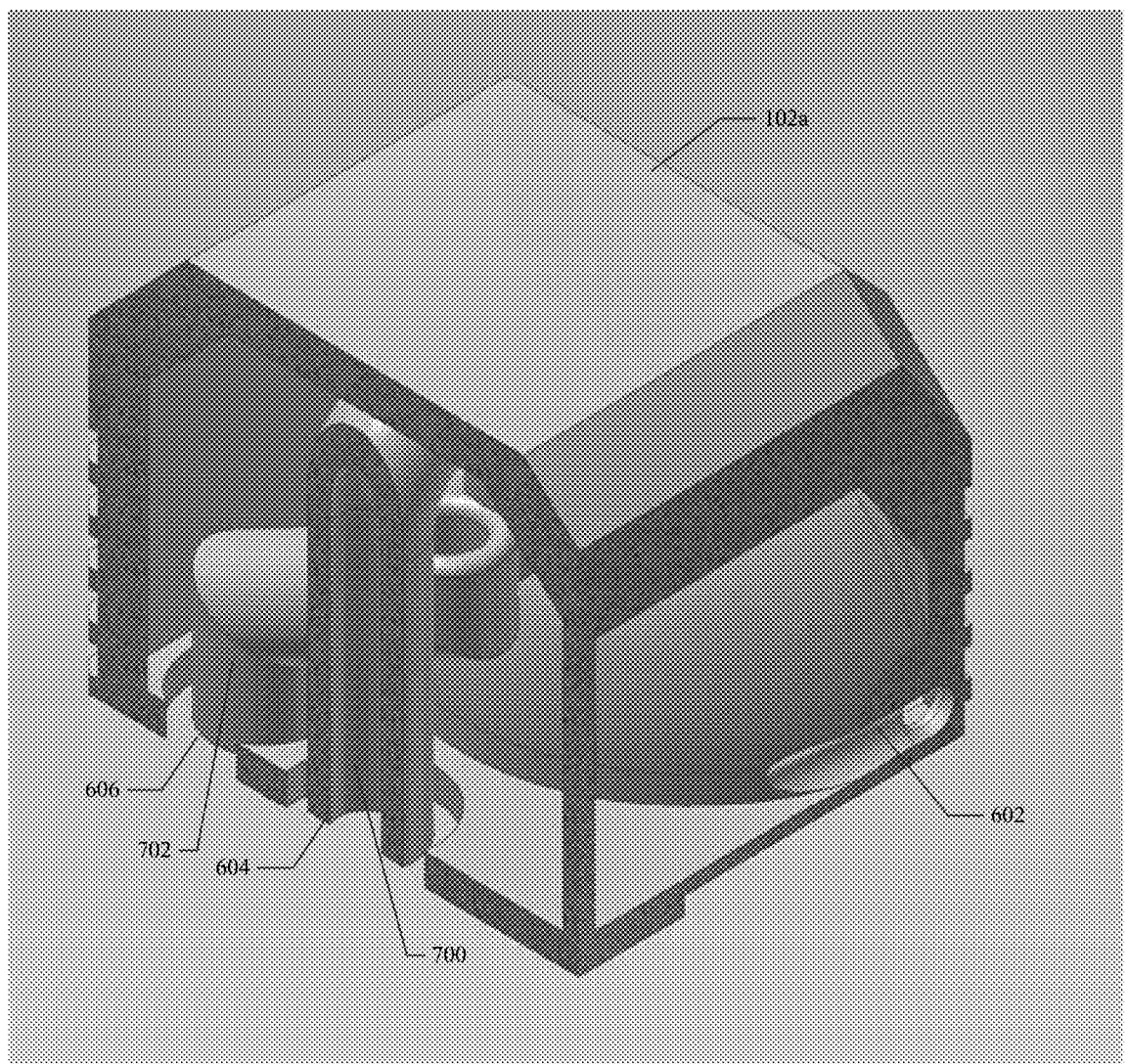
FIG. 7a depicts an interior, perspective view of an interchangeable subject interface for use with a single subject.
Figure 7B:
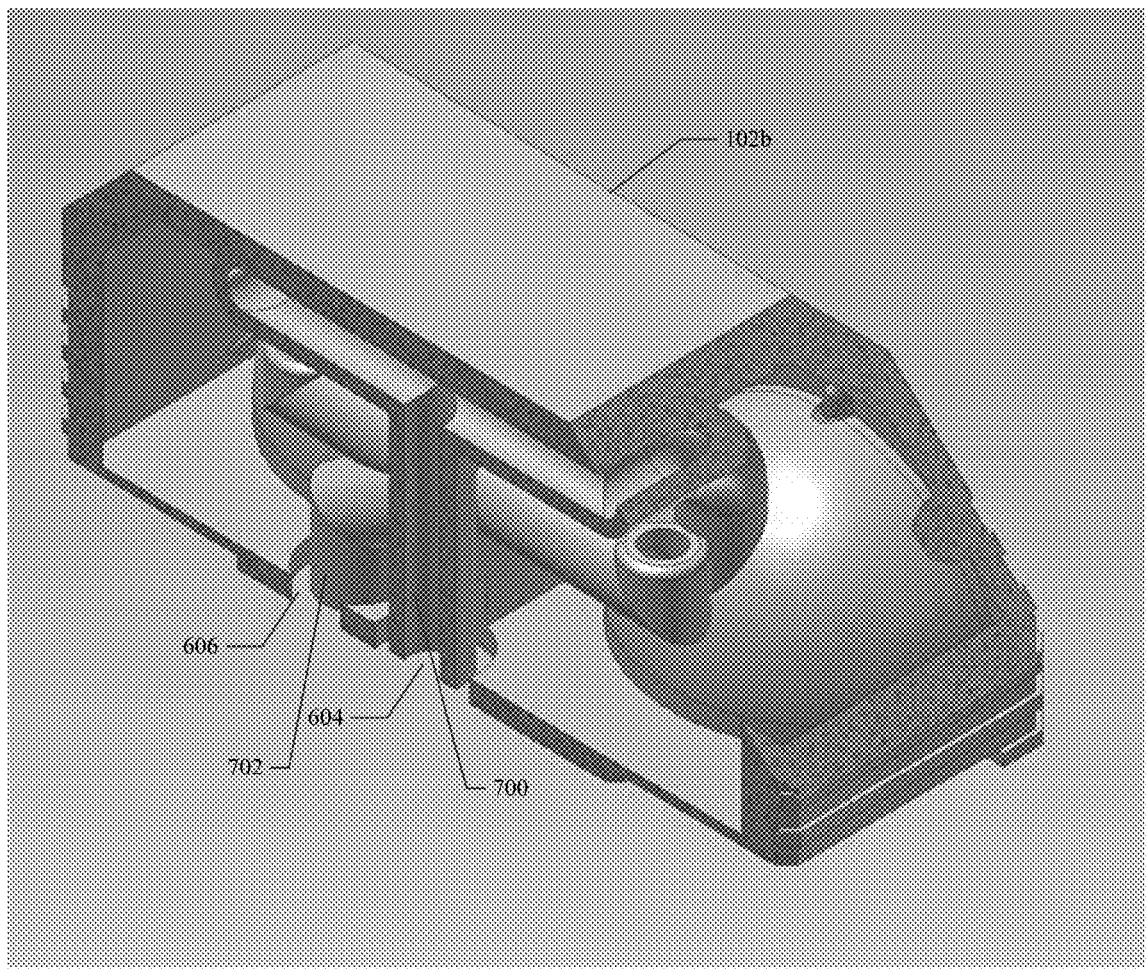
FIG. 7b depicts an interior, perspective view of an interchangeable subject interface for use with two subjects.
Figure 7C:
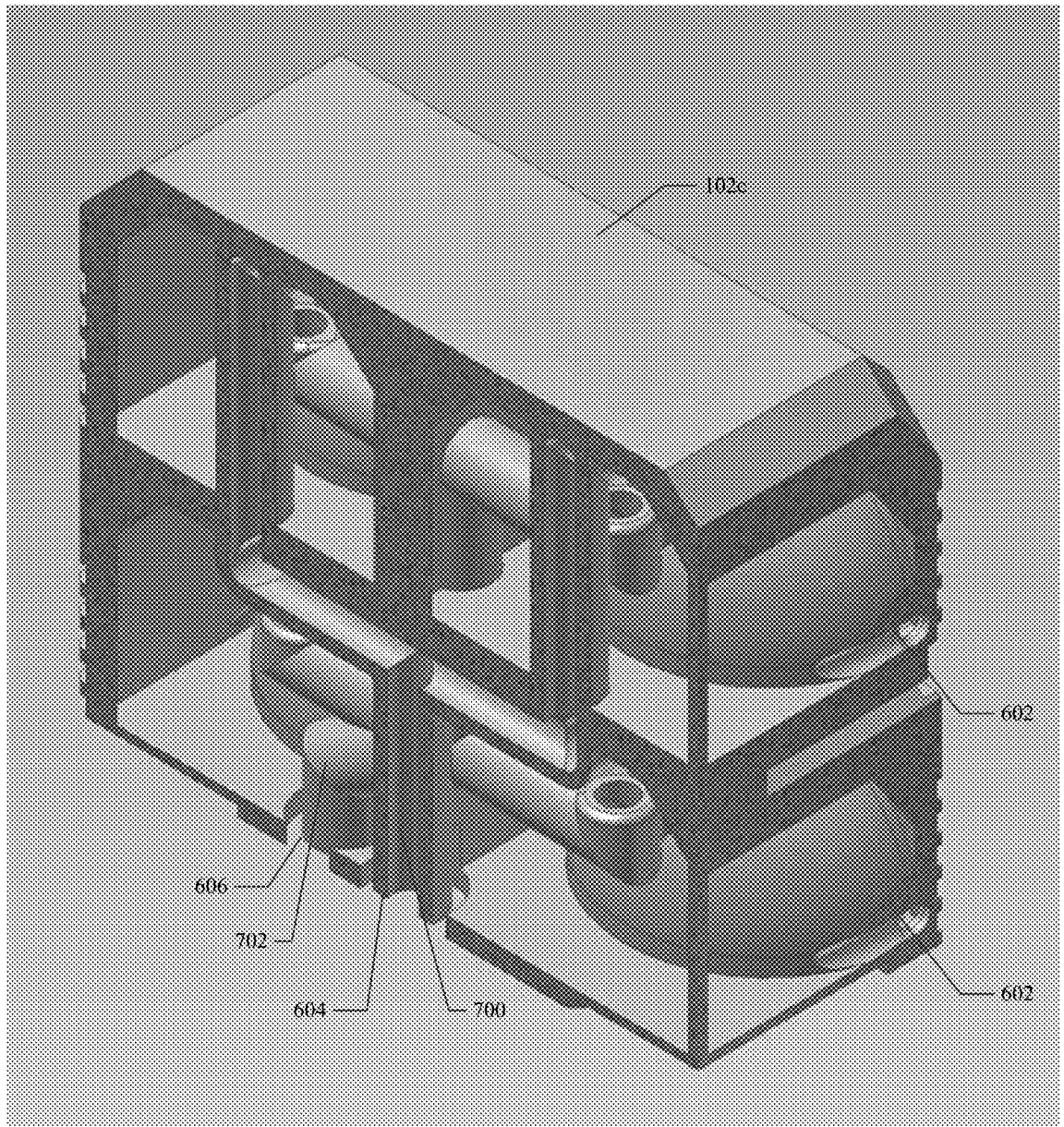
FIG. 7c depicts an interior, perspective view of an interchangeable subject interface for use with up to four subjects.

FIGS. 7a-7c depict perspective views of various configurations of the interchangeable manifolds 102a, 102b, 102c with one or more sides cut away to expose the internal lumina 700, 702 that deliver the anesthesia to the anesthesia outlet 600 and negative pressure to the exhaust inlet 602 or inlets. The anesthesia lumen 700 delivers the anesthesia to the anesthesia outlet 600 in the subject interface 200 or interfaces, while the exhaust lumen 702 draws fluid from the exhaust inlet 602. While the lumina 700, 702 are shown as tubes or pipes any configuration or shape can be used that connects the exhaust inlets 602 with the exhaust port 606 and the anesthesia outlet 600 with the anesthesia port 604.

The incorporation of the anesthesia delivery channel 800 and lumina 700 into the subject bed 100 eliminates the need for a separate tubes to connect each subject interface 200 with the anesthesia source. This integrated anesthesia channel 800 and lumina 700, 702 makes it easier to insert and remove the subject bed 100 from the imaging system, and reduces the potential for failures in the tubing or tubing connections. Consequently, the integrated anesthesia delivery apparatus is safer, more reliable and easier to use than subject bed systems with external anesthesia tubing.

Figure 8:
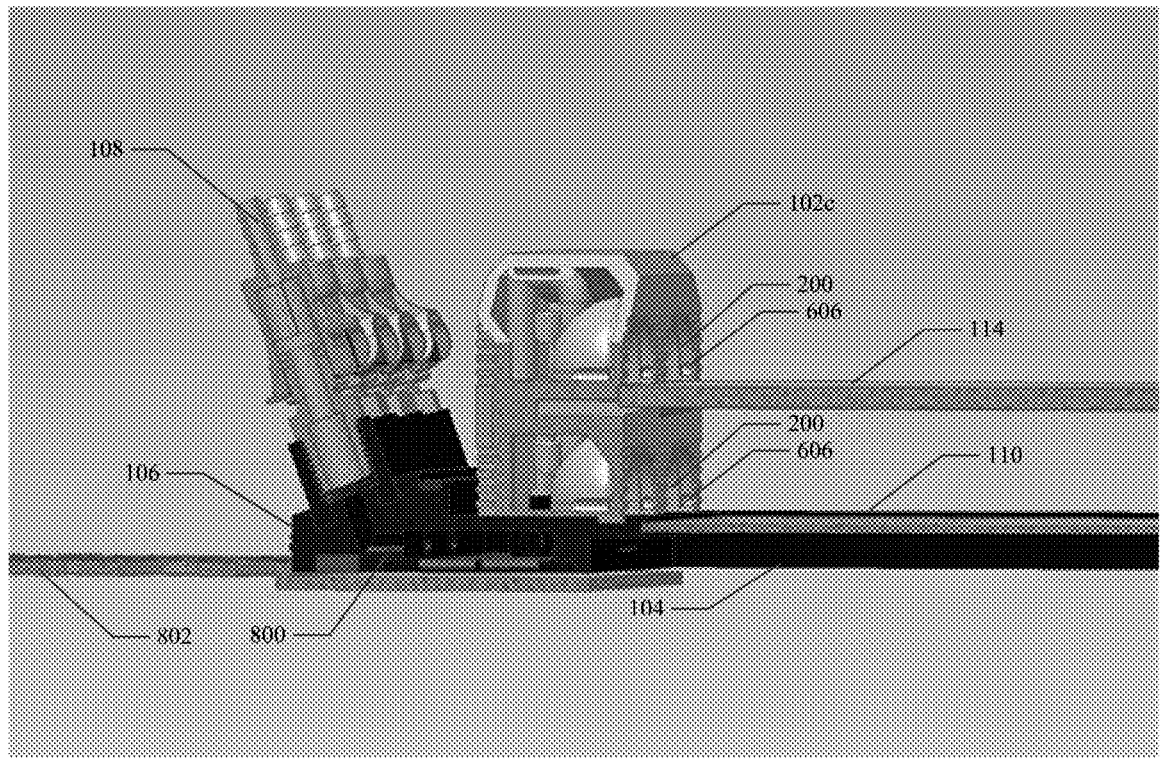
FIG. 8 depicts a side view of a subject bed with a four-subject interchangeable subject interface, elevated stage, and connectors.
Figure 9:
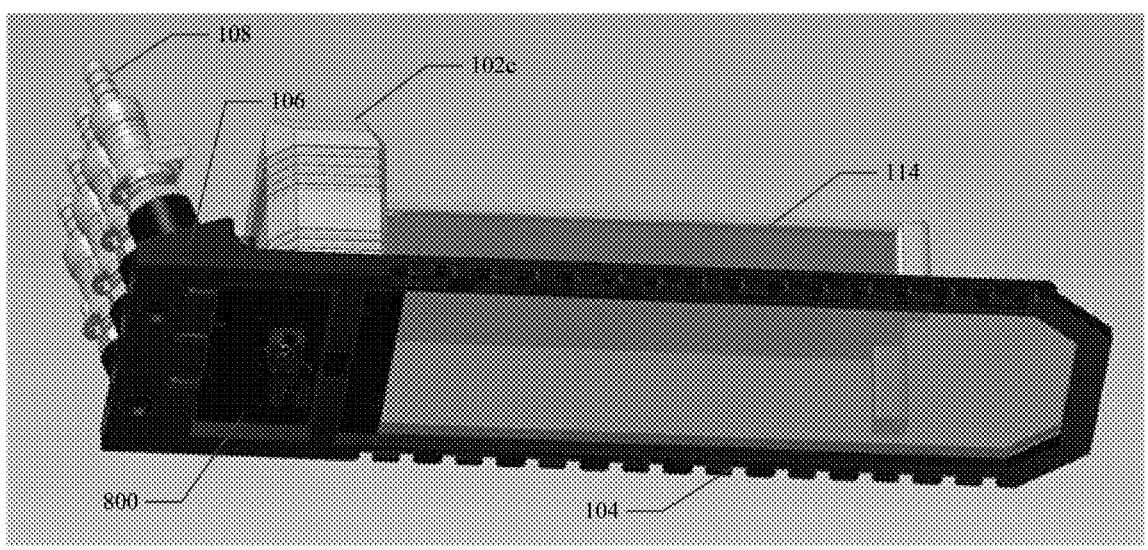
FIG. 9 depicts a perspective view of a subject bed with a four-subject interchangeable subject interface, elevated stage, and connectors.

FIG. 8 is a side view of an assembled subject bed 100 with four-subject interchangeable manifold 102c and elevated stage 114. One or more channels 800 within the base 104 connect the connector portion 106 to the exhaust port 606 and anesthesia port 604 of the manifold 102a, 102b, 102c. In other embodiments, the base 104 includes a channel 800 that directs heated fluid received from a connector via the connector portion 106 and either over the subjects on the bed surface 110, or through a portion of the base 104 below the bed surface 110 to heat the bed surface 110 and subjects.

In embodiments, the bed surface 110 is heated or cooled by fluid, such as hot or cool air, pumped into the base 104 via another connector in the connector portion 106. The fluid or air and anesthesia are exhausted or scavenged through one or more base exhaust inlets and via one or more exhaust channels in the base 104. The fluid drawn through the exhaust inlets, which can be a mixture of anesthesia, air or other fluid, is referred to herein as exhaust fluid. The exhaust fluid is drawn out through another connector by application of a vacuum to the connector.

In addition, the subject bed 100 can include an adapter 802 that attaches to the base 104 of the subject bed 100 and allows the subject bed 100 to be easily grasped either by human hands or secured to an imaging system or lab bench for surgical procedures or imaging.

In embodiments, the connectors 108 are quick-connect mechanisms that allow subject bed 100 to be quickly and easily connected and disconnected to sources for a vacuum, fluid for heating or cooling, and anesthesia. These connectors 108 facilitate preparing the subject bed 100 for insertion and removal from an imaging system, swapping out beds 100 inserted in the imaging system and speeding the process of imaging multiple subjects.

In embodiments, one or more of portions of the subject bed 100 can be composed of materials transparent to the imaging technique of the imaging system. One or more portions of the subject bed 100 can be made of chemically resistant plastics including, but not limited to, polyamides, polypropylene, polyethylene, and acrylics. Different materials may be used for different intended applications. For example, a common anesthetic is isoflurane, which degrades ABS and PLA plastics; accordingly portions of the subject bed 100 can be made either in part or entirely of an acrylic or other chemically resistant material to resist chemical deterioration. In an embodiment, the subject bed 100 and its various components can be 3D printed in optically silent material and the transparent portion of the bed surface 104 can be laser cut CLAREX plastic.

In embodiments, the subject bed 100 includes one or more fiducial receptacles or fiducial markers. In embodiments, the fiducial receptacles are shaped to receive fiducial containers, including, but not limited to, Eppendorf tubes. Such fiducial containers can be loaded with fiducial markers and easily inserted or removed from the subject bed 100. The fiducial receptacles or fiducial markers can be positioned proximate to the manifold 102a, 102b, 102c or as part of the manifold 102a, 102b, 102c. Additionally, the fiducial receptacles or fiducial markers can be positioned at any convenient location in the base 104. During imaging, fiducial markers can appear on the resulting image, allowing for calibration of the marker for later measurement. The use of removable fiducial containers allows for the quick change of fiducial markers with the subject bed 100—as may be required when using multiple imaging modalities—without disturbing the positioning of the subject or requiring cleaning of the subject bed 100 between uses. In embodiments, the fiducial receptacles are cavities in the subject bed 100 into which the fiducial containers can be inserted. In embodiments, the fiducial receptacles comprise annular rings that can support a fiducial container, such as a microcentrifuge tube.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:

1. A subject bed that supports at least one subject, comprising:
    a base having a bed surface on which the at least one subject is positioned;
    an anesthesia channel integrated into the base that receives an anesthesia fluid from an anesthesia fluid source;
    an interchangeable manifold configured to be removably attached to the base, the interchangeable manifold having at least one subject interface in fluid communication with the anesthesia channel, and the subject interface having an anesthesia outlet configured to deliver the anesthesia fluid to the at least one subject positioned on the bed surface, wherein the interchangeable manifold is a four-subject manifold; and
    an elevated stage configured to support two additional subjects and the four-subject manifold is configured to support a two-by-two array of subjects.

2. The subject bed of claim 1, wherein the interchangeable manifold is attached to the base by a magnet and can be replaced by a second interchangeable manifold to configure the subject bed for fewer than four subjects.

3. The subject bed of claim 2, wherein the second interchangeable manifold is a two-subject manifold.

4. The subject bed of claim 3, wherein the two-subject manifold is configured for side-by-side positioning of the subject and a second subject.

5. The subject bed of claim 1, wherein the elevated stage is connected to a slot in the four subject manifold.

6. The subject bed of claim 1, further comprising an exhaust channel integrated into the base, the subject interface further comprising an exhaust inlet in fluid communication with the exhaust channel, wherein negative pressure is applied to the exhaust channel to create a vacuum.

7. The subject bed of claim 6, wherein the subject interface is self-scavenging.

8. The subject bed of claim 6, wherein the exhaust inlet is proximate to an edge of the subject interface.

9. The subject bed of claim 1, further comprising a cover that mates with the base to form a chamber for the subject.

10. The subject bed of claim 1, further comprising at least one fiducial receptacle shaped to receive a removable fiducial.

11. The subject bed of claim 1, further comprising temperature control feature.

12. The subject bed of claim 1, further comprising at least one anchor point attached to the base and configured to secure the subject.

13. The subject bed of claim 1, wherein the bed surface includes a removable transparent tray.

14. A subject bed that supports at least one subject, comprising:
- a base having a bed surface on which the at least one subject is positioned and an anesthesia channel integrated into the base;
- a connector that connects an anesthesia fluid source and the anesthesia channel;
- a first detachable manifold having a first subject interface connected to the anesthesia channel, the first detachable manifold is configured to be removably detached from the base to be replaced by a second detachable manifold having a seconds, third, and fourth subject interface;
- an elevated stage configured to support two subjects side-by-side: and
- wherein each of the first, second, third, and fourth subject interfaces include an anesthesia outlet that delivers anesthesia fluid to the at least one subject, and wherein the second detachable manifold is a four-subject manifold configured to support four subjects.

15. The subject bed of claim 14, further comprising:
- an exhaust channel integrated into the base;
- an exhaust connector that connects a vacuum source to the exhaust channel; and
- at least one exhaust outlet positioned along a periphery of the subject interface, the at least one exhaust outlet connected to the exhaust channel.

* * * * *